US010354787B2

(12) United States Patent
Spearman

(10) Patent No.: US 10,354,787 B2
(45) Date of Patent: Jul. 16, 2019

(54) REMOTE CONTROLLED AND/OR TIME-LIMITED PERSONAL RESTRAINT SYSTEM

(71) Applicant: Scott Kevin Spearman, Decatur, AL (US)

(72) Inventor: Scott Kevin Spearman, Decatur, AL (US)

(73) Assignee: Scott Spearman, Decatur, AL (US)

( * ) Notice: Subject to any disclaimer, the term of this patent is extended or adjusted under 35 U.S.C. 154(b) by 200 days.

(21) Appl. No.: 15/614,538

(22) Filed: Jun. 5, 2017

(65) Prior Publication Data

US 2018/0350495 A1    Dec. 6, 2018

(51) Int. Cl.
*A61F 5/37* (2006.01)
*H01F 7/06* (2006.01)
*E05B 75/00* (2006.01)

(52) U.S. Cl.
CPC ............ *H01F 7/064* (2013.01); *A61F 5/3761* (2013.01); *E05B 75/00* (2013.01)

(58) Field of Classification Search
CPC .......... A61F 5/37; A61F 5/3761; H01F 7/064; E05B 75/00
USPC .................................................. 128/845, 869
See application file for complete search history.

(56) References Cited

U.S. PATENT DOCUMENTS

| 2005/0039499 | A1* | 2/2005 | Didomenico | B60R 99/00 70/16 |
| 2009/0211316 | A1* | 8/2009 | Butler | E05B 43/00 70/16 |
| 2011/0073118 | A1* | 3/2011 | Ponsort | A61F 5/3761 128/845 |
| 2012/0222457 | A1* | 9/2012 | Kriesel | E05B 75/00 70/16 |
| 2018/0328084 | A1* | 11/2018 | Caprino | E05B 45/06 |

* cited by examiner

*Primary Examiner* — Kristen Matter

(57) ABSTRACT

A restraining device comprised of electromagnets attached to a structure and steel pieces attached to a person's wrists that are controlled to restrain or release a person. This restraining device is wired to an enclosure with various electronic components that provide many ways of activating and deactivating the electromagnets of the restraining device. For example, it could be remotely controlled by another individual over the internet, but could also be configured to be used alone for self-restraint. A plurality of safety mechanisms, including a panic button, a countdown timer, a network polling mechanism and voice control can all be applied to make it possible for the person who is using this device to be released from their restraints.

7 Claims, 4 Drawing Sheets

REMOTE CONTROLLED AND/OR TIME-LIMITED PERSONAL RESTRAINT SYSTEM

BACKGROUND

There are times when an individual desires to be cuffed, tied, locked or otherwise restrained by another individual over a long distance. There are also times when an individual may desire to restrain themselves alone for a temporary period of time. Serious problems can arise that have traditionally been inherent in the fulfillment of these desires.

For example, In the case of individuals seeking to be remotely restrained by someone else, this has rarely if ever been done, due to the lack of an available technology, and because the practice has many inherent safety concerns for the individual being restrained.

In the case of individuals seeking to restrain themselves, this is a common practice that often results in great harm and even death to the individual.

In either situation, one of the greatest potential dangers to the individuals engaging in these practices is an inability to escape their restraints quickly and easily. Sometimes the individuals engaging in these practices cannot escape their restraints at all and they risk extreme injury or even death unless they are rescued. The apparatuses and methods outlined in this patent application provide a way for individuals seeking to engage in the above-mentioned practices to do so, and to do so safely.

BRIEF SUMMARY OF THE INVENTION

The following is intended to be a brief summary of the invention and is not intended to limit the scope of the invention.

The present invention involves both devices and methods for enabling a time-based and, when needed, a remote-controlled, restraining system.

One embodiment of the invention includes a restraining device made from a simple piece of steel and an electro-magnet, as well as a plastic holder for attaching the electro-magnet to objects and structures. The use of an electro-magnet is the linchpin of this whole design because electro-magnets require electricity to be engaged and are easy to turn on and off using electrical signals controlled by a micro-controller. In the event that the power is lost during a session, there is no risk to the individual, as this electro-magnetic restraint will release as soon as that happens.

One embodiment of the invention includes electrical cables that can be attached to the restraining device to conduct the signal that turns the electro-magnet on or off.

One embodiment of the invention includes a count-down timer controlling a relay to turn off the device when the timer reaches zero.

One embodiment of the invention includes a device or mechanism, which I call a "hub", for remotely-controlling, over a network, the activation and de-activation of the above-mentioned electro-magnetic restraining devices or other devices that may be attached.

One embodiment of the invention includes a "panic" button or switch that, when activated, can quickly turn the device off as needed.

One embodiment of the invention includes the ability to control the device, including turning it on and off, with speech and specially designated words and sounds.

One embodiment of the invention extant as part of the remote-control feature includes a mechanism in software that monitors or "pings" the remote device that is performing the remote-control activity over the network and automatically releases the electromagnetic restraints when connectivity is lost.

BRIEF DESCRIPTION OF THE DRAWINGS

A clear understanding of the key features of the invention summarized above may be had by reference to the appended drawings, which illustrate the method and system of the invention, although it will be understood that such drawings depict preferred embodiments of the invention and, therefore, are not to be considered as limiting its scope with regard to other embodiments which the invention is capable of contemplating. Accordingly:

FIG. 2 illustrates what the hub or enclosure for the device may look like.

DETAILED DESCRIPTION AND BEST MODE OF IMPLEMENTATION

The terminology used herein is for the purpose of describing particular embodiments only and is not intended to be limiting of the invention. As used herein, the term "and/or" includes any and all combinations of one or more of the associated listed items. As used herein, the singular forms "a", "an" and "the" are intended to include the plural forms as well as the singular forms, unless the context clearly indicates otherwise. It will be further understood that the terms "comprises" and/or comprising, when used in this specification specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that several techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

New remote-controlled and timer-controlled devices, apparatuses, and methods for controlling electro-magnetic restraints or locking mechanisms are discussed herein. In the following description, for purposes of explanation, numerous specific details are set forth in order to provide a thorough understanding of the present invention. It will be evident, however, to one skilled in the art that the present invention maybe practiced without these specific details.

The present disclosure is to be considered as an exemplification of the invention, and is not intended to limit the invention to the specific embodiments illustrated by the figures or description below.

The present invention will now be described by referencing the appended the figures representing preferred embodiments.

Figure 1:
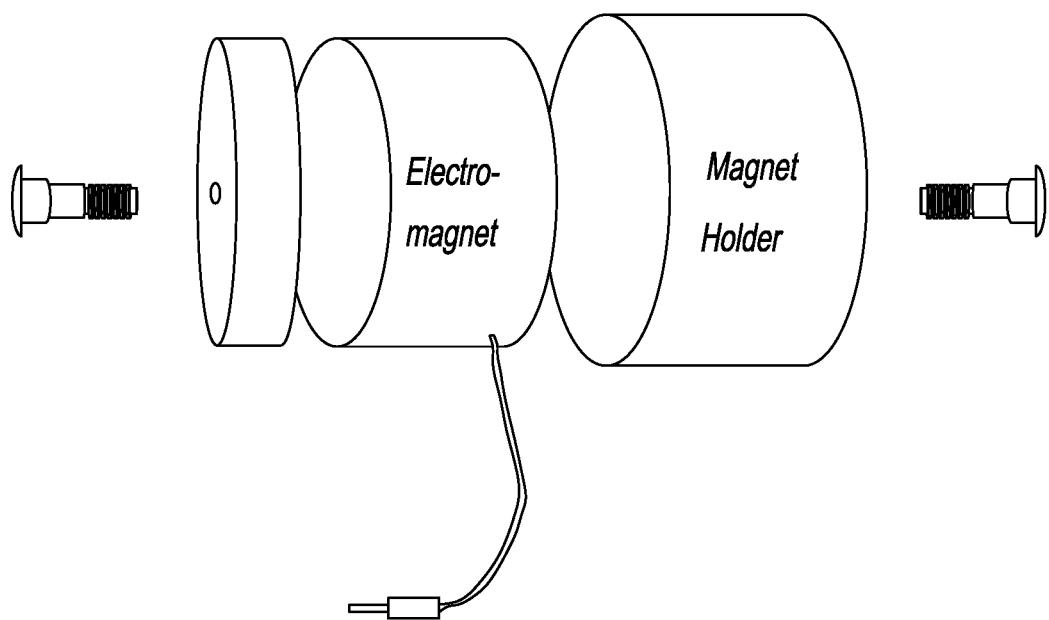
FIG. 1 shows an illustration of the electro-magnetic restraining device showing all the main embodiments, including bolts, electro-magnet holder, electro-magnet, steel piece and signal wire.

The electro-magnetic restraining device in its best implementation includes 4 parts, as shown in attached FIG. 1. The FIRST PART is a plastic holder or container for the electromagnet. This holder has two purposes, 1) to facilitate the attachment of the magnet to objects and 2) to guide the steel piece (the FOURTH PART described below) into place next to the electro-magnet. This holder is attached to the electro-magnet by means of the SECOND PART, which is a bolt, screw, eyebolt or other piece of hardware. The electro-magnet has a threaded hole to accommodate the hardware. This hardware is then used to attach the electro-magnet, to anything the user desires. Some usage examples include attaching the electro-magnet with the hardware to a) a piece a furniture, b) a wall, c) a fence, d) a length of chain, e) a length of rope or f) a piece of wood. The THIRD PART is the electromagnet itself. The electro-magnet will have wires coming out of it for conducting the electrical signal that is used to turn the magnets on and off. In the best implementation, those wires will be terminated to a port, such as an audio signal port or power port. The FOURTH PART is a simple piece of steel or iron to engage with the electromagnet. This steel piece is of the proper size and shape to fit closely against the electro-magnet so that when the magnet is engaged it is very difficult, if not impossible, for the steel piece to be removed. This steel piece can easily be guided into place properly next to the electro-magnet by means of the plastic holder. The steel piece also has a threaded hole to accommodate PART FIVE, which is hardware such as nuts, bolts or eyebolts. The steel piece is attached by means of this hardware to the actual device restraining the individual, such as a wrist cuff, ankle cuff or a length of rope tied securely to the user's wrists or ankles.

This invention requires the use of cables used to carry the signals from the main "hub" to the electro-magnets to turn them on and off. These cables would have connectors at each end that fit the ports on the electro-magnet and hub.

Figure 2:
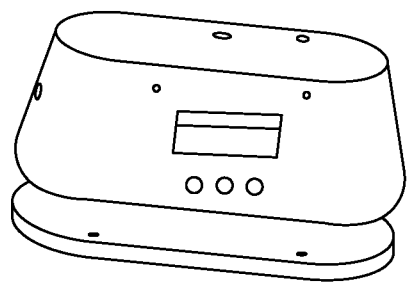
Figure 2:
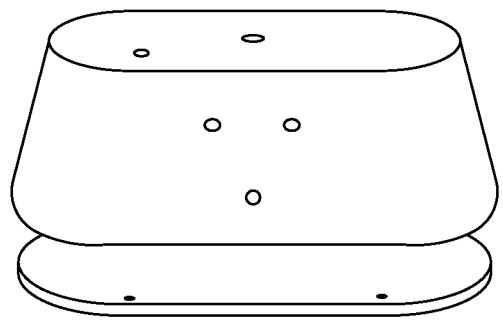

This invention has a "hub" or enclosure. An example of this hub or enclosure is shown in FIG. 2. The "hub" has external ports that are used to attach various components. These components include the following: a) the cables from the electro-magnets, for which there would be at least two ports, b) a DC Power supply, for which there is one port, c) a "panic" button or switch, for which there is one port and d) possibly other ports with which to attach other devices that the user wishes to control using the micro-controller. (These possible other devices are not an embodiment of this patent). The exterior of the hub also has a digital timer display and buttons for setting and controlling the timer and, therefore, the whole device.

Inside the hub are numerous electrical and electronics components, including one or more micro-controllers, a countdown timer, buttons for setting and controlling the timer and multiple electrical relays used to turn various devices, such as the electro-magnets, on and off. Fundamentally, the components inside the "hub" contain a series of cascading and interdependent electrical circuits that are used to power and control the operations of this invention. These circuits are separated to provide the required safety components of the invention, and each one will be described separately.

Power Supply and Panic Button—

Figure 3:
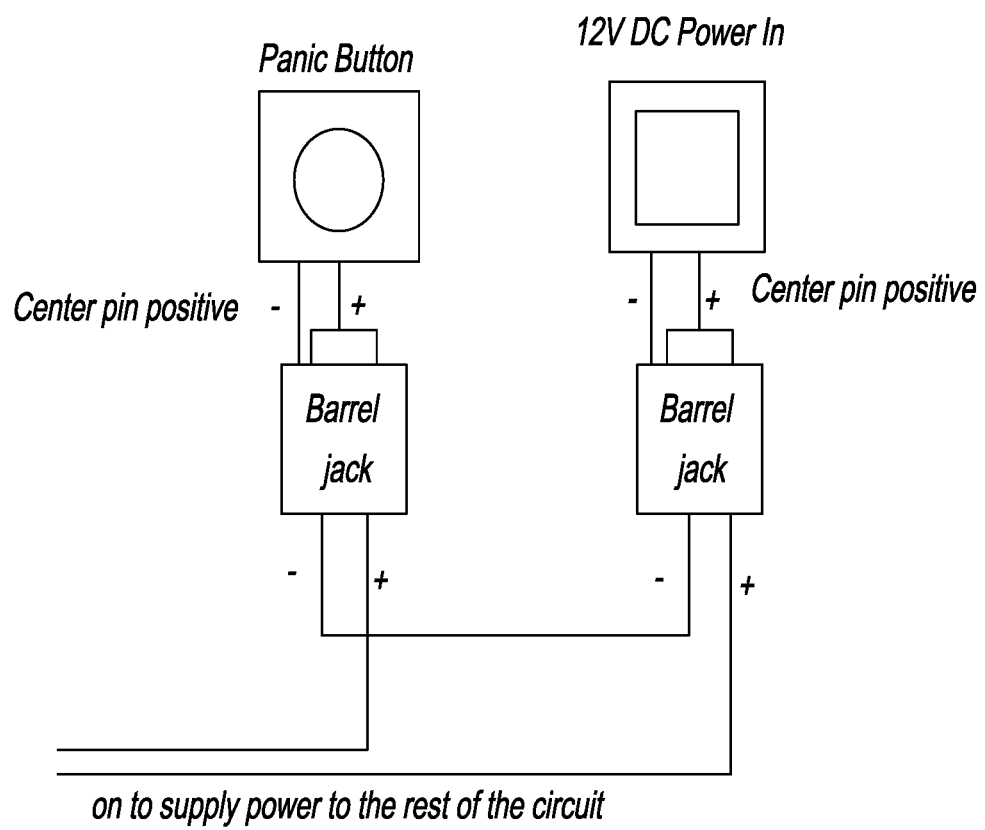
FIG. 3 presents a diagram of the main power input circuit including the "panic" button or switch.

The first circuit encompasses the incoming DC power supply and the "panic" button or switch. This circuit is illustrated in FIG. 3. This is wired in such a way so that the entire device cannot be turned on unless BOTH the device is plugged into the power supply AND the "panic" button is enabled. The panic button is attached to a long cable and is placed in a location close to the hand of the individual being restrained, such that if the individual turns the switch off, the device is powered off and the electro-magnets are released. This is the first circuit and it is a simple one-source, one-load circuit controlled by a SPST switch, the "panic" button.

Count-Down Timer Safety Module—

Figure 4:
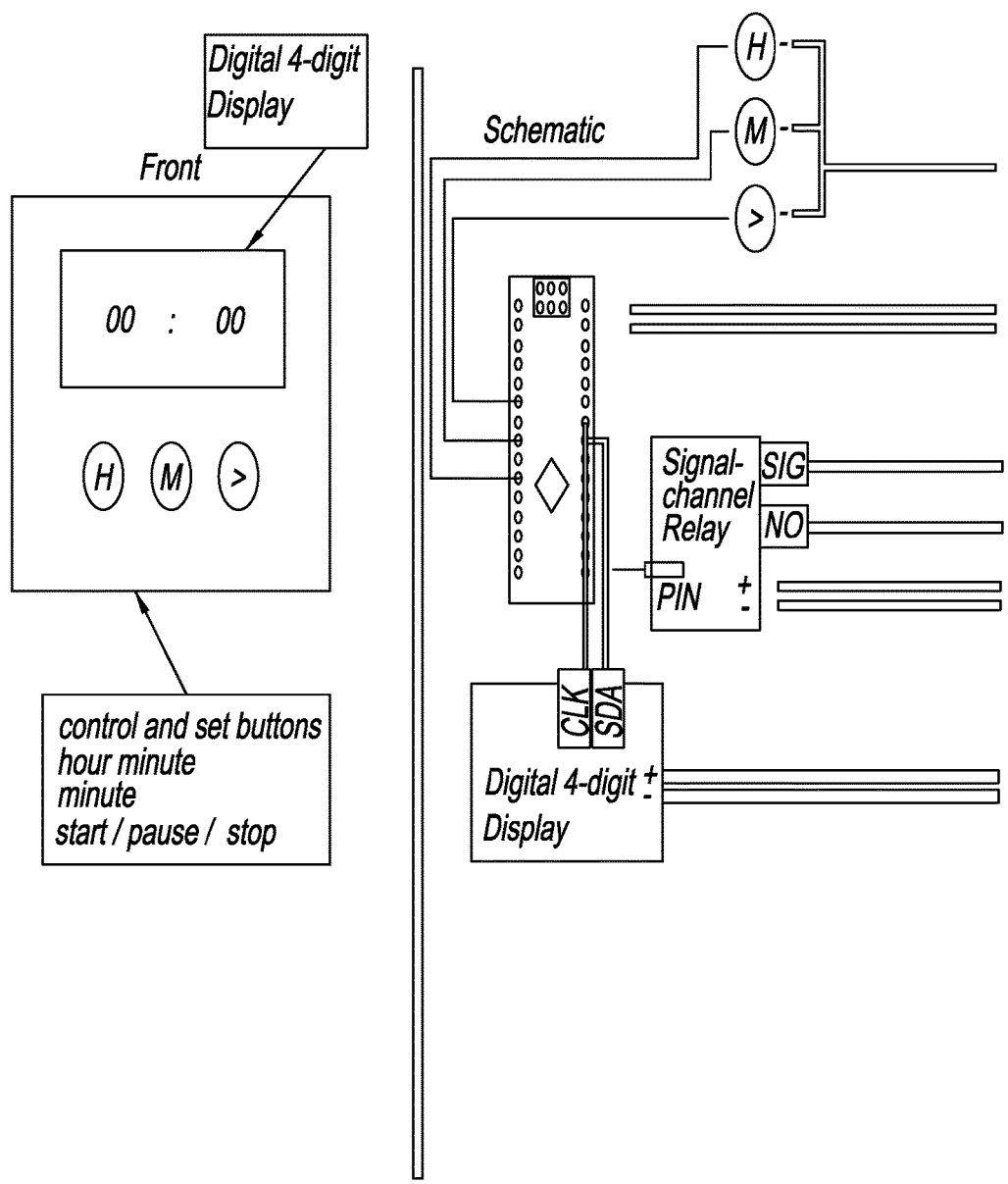
FIG. 4 presents a diagram of the countdown timer module circuit.

The second primary circuit, created to supply another safety feature, is the Timer Module. This circuit is illustrated in FIG. 4. If the first circuit is turned on, then the power, which in my example is 12V DC, is split to two loads 1) 12V can be attached to the Timer relay to be supplied to the main unit and 2) 12V is supplied to a 12 VDC to 5 VDC converter that is used to power the microcontroller, timer and buttons, which are 5 V devices. The Timer module is comprised of a) a microcontroller running the timer software, b) a display such as a matrix display or 7-segment multi-digit display, c) buttons for controlling the display and timer module and d) a relay to enable and disable power to the main unit. The Timer circuit provides the function of time-limiting the use of the device. And is used this way. After the user has plugged in the power and actuated the panic button, power is supplied to the timer module. The timer module has three buttons designated HOUR, MINUTE and START/PAUSE/STOP. The user will use the buttons to enter a time denoting hours and/or minutes and then press the Start button. When s/he does so, the timer module will actuate the local relay, which is NORMALLY OPEN and the circuit will turn on and supply power to the main module. When the timer reaches zero, the Timer Module will open the relay and cut power to the main module, thereby freeing the user from the electro-magnetic restraints. In the use case where the user of the device is using it by themselves and is not being remote-controlled by another individual, then a feature implemented in software is to manipulate the buttons in such a way that the activation of the electro-magnetic restraints is delayed for a short period of time, such as a minute or two. This gives the user time to get into place and insert the steel piece into the holder before the electromagnet is engaged. Other functionality may be added to the timer module as needed, but this function of supplying and cutting power to the main module and the electro-magnetic restraint system using a count-down timer function, is its primary purpose.

Main Relay Module—

Figure 5:
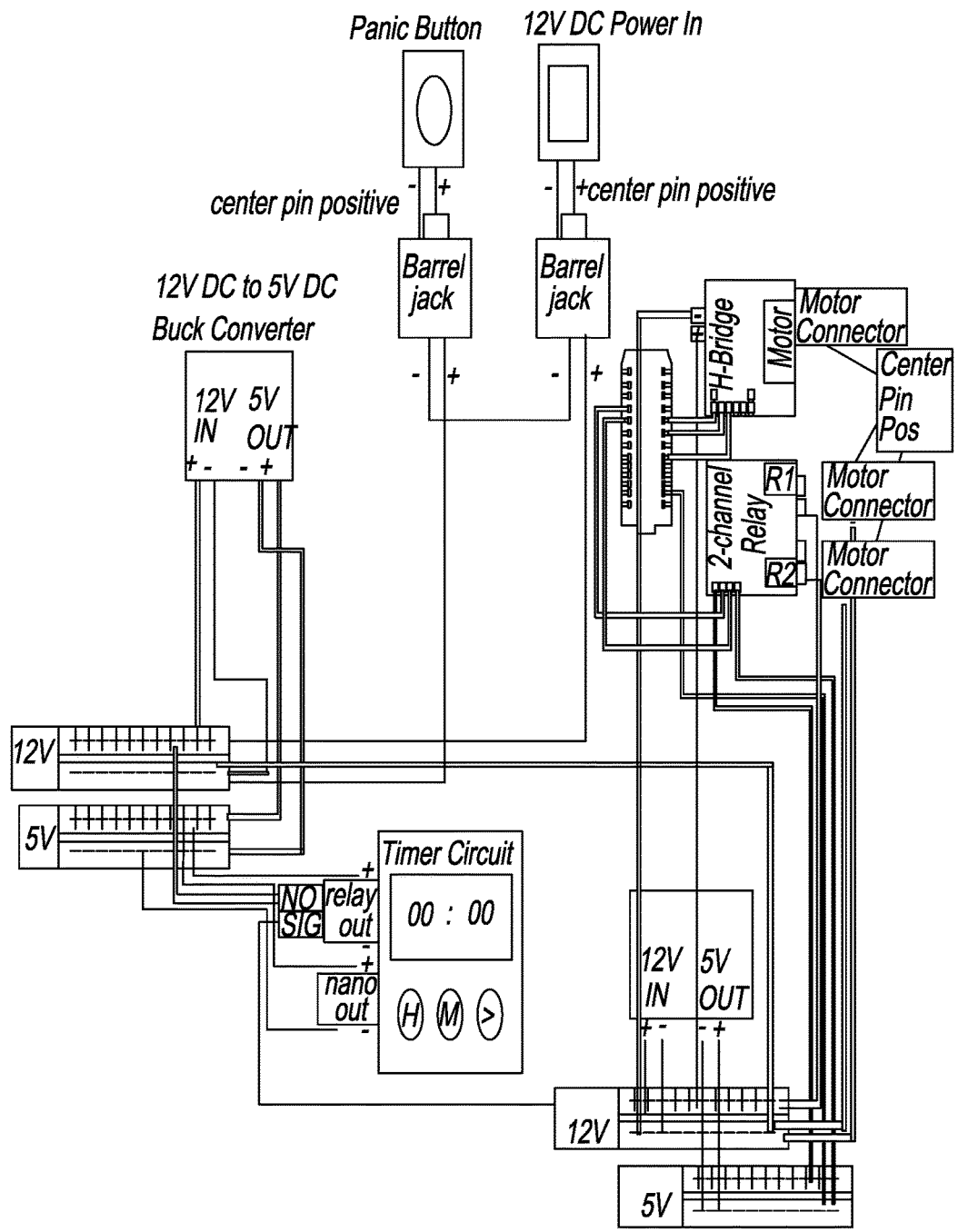
FIG. 5 presents a diagram of the entire Circuit and Microcontroller for remotely controlling or timer-limiting the electro-magnetic restraints.

The Final module in the invention is the main relay module controlling the electro-magnetic restraint devices. This circuit is illustrated in FIG. 5. The 12 V DC power coming from the timer relay is split to two loads 1) 12V can be attached directly to the relays used to control the electro-magnetic restraints 2) 12V is supplied to a 12 VDC to 5 VDC converter that is used to power the microcontroller. This microcontroller provides 3 important capabilities.

First, it has output pins that are used to turn the relays on and off for enabling and disabling the electro-magnetic restraining devices. The relays are NORMALLY OPEN and these output pins, will send a signal, such as a change from low to high voltage, that will then actuate the relay and engage the attached electro-magnets. Conversely, when the pin changes the signal in the opposite direction, for example from high to low, then the relay is set back to open and the electro-magnetic restraints are released. Ideally, there should be one pin, one signal and one relay and one port for each attached electro-magnetic restraint, although it may be possible to have more attached using splitters. Additionally, The microcontroller will likely have additional output pins which could be used to control other devices that are outside the scope of this patent.

Second, this microcontroller has capabilities through embedded software that enable it to connect to a local network or the internet so that the various pins can be controlled remotely from another device, such as a cellphone, computer, tablet or microcontroller. This part of the invention's functionality will make extensive use of prior-art, such as networking capabilities, wi-fi, internet protocols, security features, etc.

Third, embedded Software in the microcontroller will perform another important safety function. Namely, it will maintain constant contact with the remotely controlling device by polling or "pinging" it every few seconds and verifying that the connection is still available and working. If this device loses the connection to the remote device and is unable to poll it, after a time-out period the software will send the appropriate signal to the relay pins to disengage the relays and release the electro-magnetic restraints. This will prevent the device user from becoming stuck in the restraints in the event of a network outage or if the remote device becomes disconnected.

Another embodiment of this device is the use of voice-activated AI to control the device. This embodiment would likely make extensive use of AI and Speech-recognition prior art and could be implemented outside the device as a standalone power control hub, or it could be implemented in software in the primary microcontroller or in the timer microcontroller. This embodiment would require the use of additional hardware not described in detail in this patent, such as microphones and AI controlled microcomputers.

Device Use Case 1

While the invention is powered up, with the panic button engaged, the timer module active and power being relayed to the main module, then another individual can control the microcontroller and any attached devices, in particular the electro-magnetic restraint devices, remotely. They will be able, with the consent of the device user, to remotely control the restraint devices (and possibly other devices outside the scope of this patent.) Even so, the device user will still be able to make use of other embodiments of this patent, such as the timer, voice-activated AI and panic button to release the electro-magnetic restraints. Plus, the software polling feature will be in use to provide additional safety.

Device Use Case 2—

For solo users, while the invention is powered up, with the panic button engaged, the timer module active and power being relayed to the main module, an individual can restrain themselves if they desire. In this case, the user would activate the timer and indicate this is a self-restraint situation and the software would activate a delay of a minute or two until it activates the electro-magnets. This will give the solo user time to get into place and get the steel pieces attached and in place in the plastic holder. Once the solo timer reaches zero, the relays are engaged and the pre-programmed countdown begins the user's self-restraint session. During this self-restraint session, the solo device user will still be able to make use of other embodiments of this patent, such as the panic button or voice-activated AI, to release the electro-magnetic restraints

What is claimed is:

1. A remote controlled and time-limiting restraint system comprising:
   an electromagnet, the electromagnet being attached to an immovable object or piece of furniture by a fastener, the electromagnet further being configured to release a restrained person in the event of a power failure;
   a piece of steel for magnetically attaching to the electromagnet, the piece of steel being attached to a restraining device for restraining the person;
   an enclosure housing electronics for controlling the electromagnet;
   a power source for providing power to the electronics;
   a controller programmed to enable remote control of the electronics over a network;
   a manual safety mechanism configured to enable the restrained person to cut power to the electromagnet for releasing the restrained person; and
   a countdown timer that automatically cuts power to the electromagnet when the timer expires in order to release the restrained person.

2. The system of claim 1, wherein the manual safety mechanism is a button or switch configured to be operated by the restrained person.

3. The system of claim 1, wherein the manual safety mechanism comprises a microphone for recognizing speech and sounds for cutting power to the electromagnet.

4. The system of claim 1, wherein the controller is further programmed with a built-in delay before activating the electromagnet.

5. The system of claim 1, wherein the controller is further programmed to cut power to the electromagnet when it is determined that a connection to the network has been lost.

6. The system of claim 1, wherein the fastener is a screw or bolt.

7. A remote controlled and time-limiting restraint system comprising:
   a device attached to a restraining device for restraining a person, the device further attached to an immovable object or piece of furniture by a fastener;
   an enclosure housing electronics that control the device;
   a power source for providing power to the electronics;
   a controller programmed to enable remote control of the electronics over a network;
   a manual safety mechanism configured to enable the restrained person to deactivate the restraining device for releasing the restrained person; and
   a countdown timer that automatically cuts power to the device when the timer expires in order to release the restrained person.

* * * * *